US011617582B2

(12) United States Patent
Marecki et al.

(10) Patent No.: US 11,617,582 B2
(45) Date of Patent: Apr. 4, 2023

(54) SURGICAL RELOADABLE CARTRIDGE ASSEMBLY

(71) Applicant: Lexington Medical, Inc., Billerica, MA (US)

(72) Inventors: Andrew Marecki, West Boylston, MA (US); Otto Briner, Somerville, MA (US); Leon Amariglio, Lexington, MA (US)

(73) Assignee: Lexington Medical, Inc., Bedford, MA (US)

( * ) Notice: Subject to any disclaimer, the term of this patent is extended or adjusted under 35 U.S.C. 154(b) by 99 days.

(21) Appl. No.: 17/033,210

(22) Filed: Sep. 25, 2020

(65) Prior Publication Data

US 2021/0007740 A1 Jan. 14, 2021

Related U.S. Application Data

(62) Division of application No. 15/631,429, filed on Jun. 23, 2017, now Pat. No. 10,912,560.

(51) Int. Cl.
*A61B 17/072* (2006.01)
*A61B 17/068* (2006.01)
*A61B 17/064* (2006.01)
*A61B 17/00* (2006.01)

(52) U.S. Cl.
CPC ...... *A61B 17/07207* (2013.01); *A61B 17/064* (2013.01); *A61B 17/068* (2013.01); *A61B 2017/00473* (2013.01); *A61B 2017/07285* (2013.01)

(58) Field of Classification Search
CPC ............ A61B 17/07207; A61B 17/068; A61B 17/064; A61B 2017/00473; A61B 2017/07285
See application file for complete search history.

(56) References Cited

U.S. PATENT DOCUMENTS

| 4,978,049 | A |   | 12/1990 | Green |                |
|-----------|---|---|---------|----------|----------------|
| 5,322,161 | A | * | 6/1994  | Shichman | ...... A61B 50/30 |
|           |   |   |         |          | 206/204        |
| 5,325,987 | A | * | 7/1994  | Alpern   | ...... B65D 81/022 |
|           |   |   |         |          | 206/370        |

(Continued)

FOREIGN PATENT DOCUMENTS

| CN | 1985768   | 6/2007 |
|----|-----------|--------|
| CN | 101194853 | 6/2008 |

(Continued)

OTHER PUBLICATIONS

International Search Report and Written Opinion dated Oct. 22, 2018 for PCT Application No. PCT/US2018/038909 Filed Jun. 22, 2018, 10 pages.

(Continued)

*Primary Examiner* — Thomas M Wittenschlaeger
(74) *Attorney, Agent, or Firm* — Brooks, Cameron & Huebsch, PLLC

(57) ABSTRACT

The present disclosure includes apparatuses for a surgical reloadable cartridge assembly. An example apparatus includes a lock slider and a blade lock configured to actuate radially between a first position that locks a blade in a secure position and a second position that allows the blade to move longitudinally.

17 Claims, 6 Drawing Sheets

SECTION E-E

(56) References Cited

U.S. PATENT DOCUMENTS

| | | | |
|---|---|---|---|
| 5,326,013 A | 7/1994 | Green et al. | |
| 5,379,895 A * | 1/1995 | Foslien | A61B 50/30 206/363 |
| 5,453,094 A * | 9/1995 | Metcalf | A61B 17/3417 206/571 |
| 5,507,426 A | 4/1996 | Young et al. | |
| 5,651,491 A * | 7/1997 | Heaton | A61B 17/07207 227/176.1 |
| 5,762,256 A | 6/1998 | Mastri et al. | |
| 5,865,361 A | 2/1999 | Milliman et al. | |
| 5,901,895 A | 5/1999 | Heaton et al. | |
| 6,109,500 A | 8/2000 | Alli et al. | |
| 7,044,352 B2 | 5/2006 | Shelton, IV et al. | |
| 7,044,353 B2 | 5/2006 | Mastri et al. | |
| 7,097,089 B2 | 8/2006 | Marczyk | |
| 7,143,923 B2 | 12/2006 | Shelton, IV et al. | |
| 7,143,924 B2 | 12/2006 | Scirica et al. | |
| 7,225,963 B2 | 6/2007 | Scirica | |
| 7,380,695 B2 | 6/2008 | Doll et al. | |
| 7,624,902 B2 | 12/2009 | Marczyk et al. | |
| 7,694,865 B2 | 4/2010 | Scirica | |
| 7,780,055 B2 | 8/2010 | Scirica et al. | |
| 7,837,079 B2 | 11/2010 | Holsten et al. | |
| 7,845,535 B2 | 12/2010 | Scircia | |
| 7,900,805 B2 * | 3/2011 | Shelton, IV | A61B 17/07207 227/176.1 |
| 7,963,431 B2 | 6/2011 | Scirica | |
| 7,967,180 B2 | 6/2011 | Scirica | |
| 8,056,789 B1 | 11/2011 | White et al. | |
| 8,157,148 B2 | 4/2012 | Scirica | |
| 8,336,751 B2 | 12/2012 | Scirica | |
| 8,336,754 B2 * | 12/2012 | Cappola | A61B 17/07207 227/19 |
| 8,584,919 B2 * | 11/2013 | Hueil | A61B 17/07207 227/176.1 |
| 8,608,043 B2 | 12/2013 | Scirica | |
| 8,632,535 B2 * | 1/2014 | Shelton, IV | A61B 17/00 606/1 |
| 8,695,865 B2 | 4/2014 | Smith et al. | |
| 9,072,523 B2 * | 7/2015 | Houser | H02J 7/025 |
| 9,089,338 B2 * | 7/2015 | Smith | A61B 18/12 |
| 9,241,715 B2 * | 1/2016 | Kasvikis | A61B 17/068 |
| 9,844,378 B2 * | 12/2017 | Casasanta | A61B 17/068 |
| 9,855,040 B2 * | 1/2018 | Kostrzewski | A61B 17/42 |
| 10,039,546 B2 * | 8/2018 | Williams | A61B 17/1155 |
| 10,849,621 B2 * | 12/2020 | Whitfield | A61B 90/03 |
| 2005/0116009 A1 | 6/2005 | Milliman | |
| 2006/0079912 A1 | 4/2006 | Whitfield et al. | |
| 2008/0017693 A1 | 1/2008 | Mastri et al. | |
| 2008/0083810 A1 | 4/2008 | Marczyk | |
| 2008/0179374 A1 | 7/2008 | Beardsley et al. | |
| 2009/0062614 A1 | 3/2009 | Adzich et al. | |
| 2009/0145947 A1 | 6/2009 | Scirica | |
| 2010/0001036 A1 | 1/2010 | Marczyk et al. | |
| 2010/0264193 A1 | 10/2010 | Huang et al. | |
| 2011/0290854 A1 * | 12/2011 | Timm | A61B 17/07207 227/178.1 |
| 2012/0053406 A1 * | 3/2012 | Conlon | A61B 17/29 606/49 |
| 2012/0111591 A1 * | 5/2012 | Shelton, IV | A61B 18/12 206/723 |
| 2012/0286019 A1 * | 11/2012 | Hueil | A61B 17/07207 227/175.1 |
| 2013/0092719 A1 | 4/2013 | Kostrzewski | |
| 2013/0304115 A1 | 11/2013 | Miyamoto | |
| 2014/0224856 A1 | 8/2014 | Smith et al. | |
| 2015/0083738 A1 * | 3/2015 | Kasvikis | A61B 17/07207 220/694 |
| 2015/0374396 A1 | 12/2015 | Strobl et al. | |
| 2016/0058441 A1 | 3/2016 | Morgan et al. | |
| 2018/0289370 A1 | 10/2018 | Amariglio et al. | |

FOREIGN PATENT DOCUMENTS

| | | |
|---|---|---|
| CN | 101965156 | 2/2011 |
| EP | 1563791 | 8/2005 |
| EP | 1563792 | 8/2005 |
| EP | 1563794 | 8/2005 |
| EP | 1709911 | 10/2006 |
| EP | 1021130 | 11/2006 |
| EP | 1908410 | 4/2008 |
| EP | 2253277 | 11/2010 |
| EP | 2253278 | 11/2010 |
| EP | 2586382 | 9/2013 |
| EP | 2777530 | 9/2014 |
| EP | 2886071 | 6/2015 |
| WO | 2016/107586 | 7/2016 |

OTHER PUBLICATIONS

CN First Office Action dated Feb. 28, 2020 for CN Application No. 201880022626.9 Filed Sep. 27, 2019, 14 pages.

International Search Report and Written Opinion dated Apr. 7, 2020 for PCT Application No. PCT/US2020/013694 filed Jan. 15, 2020, 8 pages.

European Search Report and Opinion for related EP Application No. 18821325.0, dated Oct. 19, 2020, 10 pages.

* cited by examiner

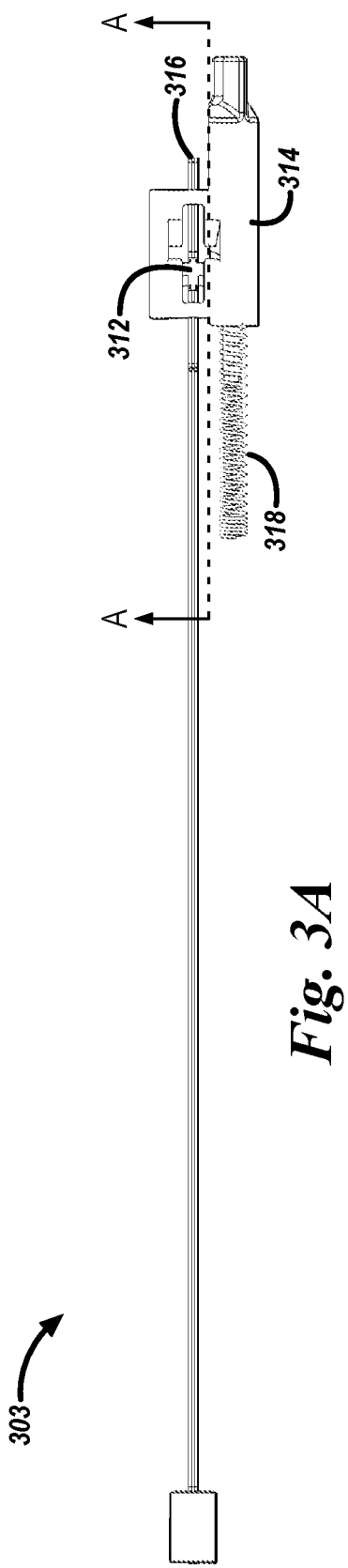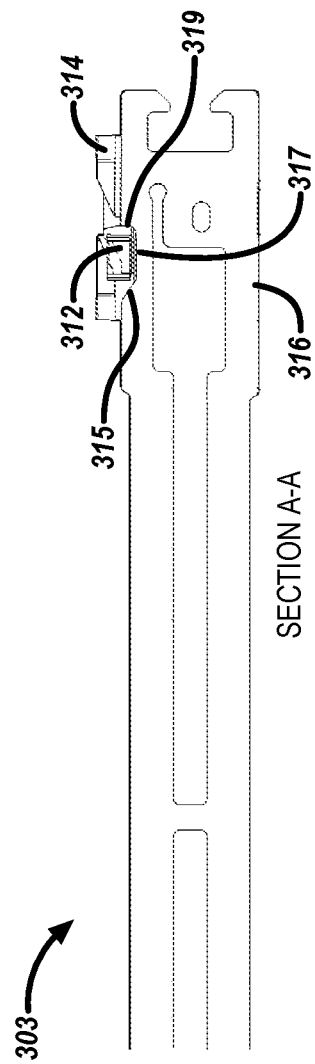
*Fig. 3A*
*Fig. 3B*

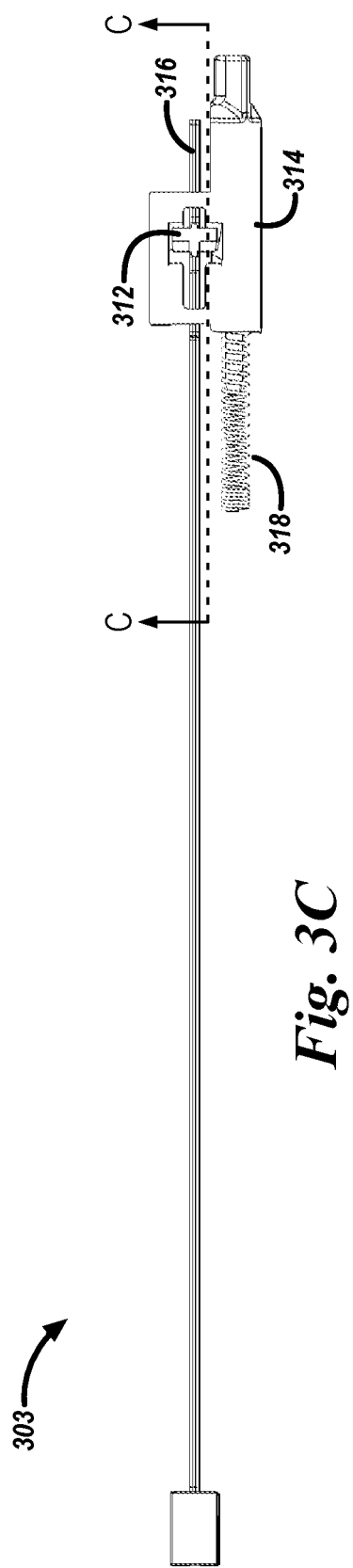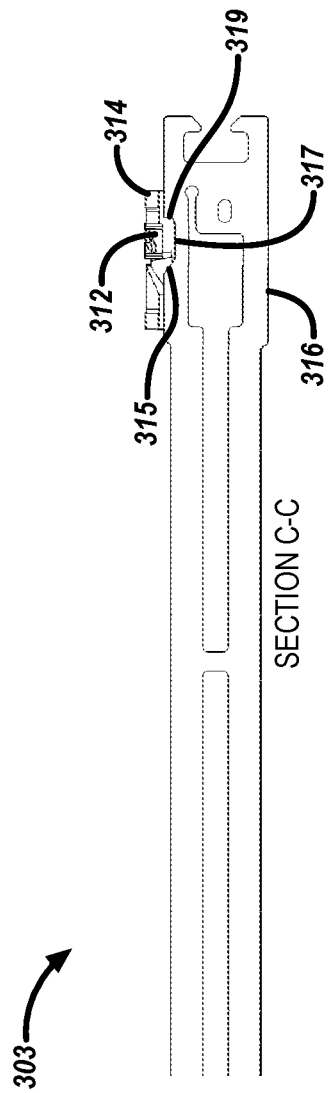
Fig. 3C
Fig. 3D

SURGICAL RELOADABLE CARTRIDGE ASSEMBLY

CROSS REFERENCE TO RELATED APPLICATION

This application is a divisional of U.S. application Ser. No. 15/631,429, filed Jun. 23, 2017, the entire specification of which is incorporated herein by reference.

TECHNICAL FIELD

The present disclosure relates generally to a surgical reloadable cartridge assembly, and more particularly, to a surgical reloadable cartridge assembly comprising a lock slider and a blade lock.

BACKGROUND

A surgical reloadable cartridge assembly can be used in a number of surgical devices. One example includes use as a surgical stapler. A surgical stapler is a fastening device used to clamp tissue between opposing jaw structures to join tissue using surgical fasteners. Surgical staplers can include two elongated members used to clamp the tissue. One of the elongated members can include one or more staple cartridges and the other elongated member can include an anvil that can be used to form a staple when driven from the staple cartridge. An example of a staple cartridge assembly can include having rows of staples having a linear length. For example, a row of staples can have a linear length between 30 mm and 60 mm. The surgical stapler can include a surgical handle assembly connected to the surgical reloadable cartridge assembly. A staple can be ejected by actuation of a movable handle member that is a part of the surgical handle assembly of the surgical stapler.

A surgical stapler can receive one or more surgical reloadable cartridge assemblies. An example of a surgical reloadable cartridge assembly can include an articulation arm and a blade. The articulation arm can facilitate access to tissue by pivoting the jaw structures. The blade can facilitate clamping of the tissue when the movable handle member is actuated. The blade can also actuate the ejection of staples when the movable handle member is actuated.

The blade included in the surgical reloadable cartridge assembly can form an incision in tissue. For example, the blade can longitudinally cut and/or open stapled tissue. An example of a surgical reloadable cartridge assembly can include a blade that cuts tissue between rows of staples.

BRIEF DESCRIPTION OF THE DRAWINGS

FIG. 3A is a schematic diagram of a surgical reloadable cartridge assembly including a blade lock in a first position in accordance with a number of embodiments of the present disclosure.

FIG. 3B is a section view schematic diagram of a surgical reloadable cartridge assembly including a blade lock in a first position in accordance with a number of embodiments of the present disclosure.

FIG. 3C is a schematic diagram of a surgical reloadable cartridge assembly including a blade lock in a second position in accordance with a number of embodiments of the present disclosure.

FIG. 3D is a section view schematic diagram of a surgical reloadable cartridge assembly including a blade lock in a second position in accordance with a number of embodiments of the present disclosure.

DETAILED DESCRIPTION

Figure 1:
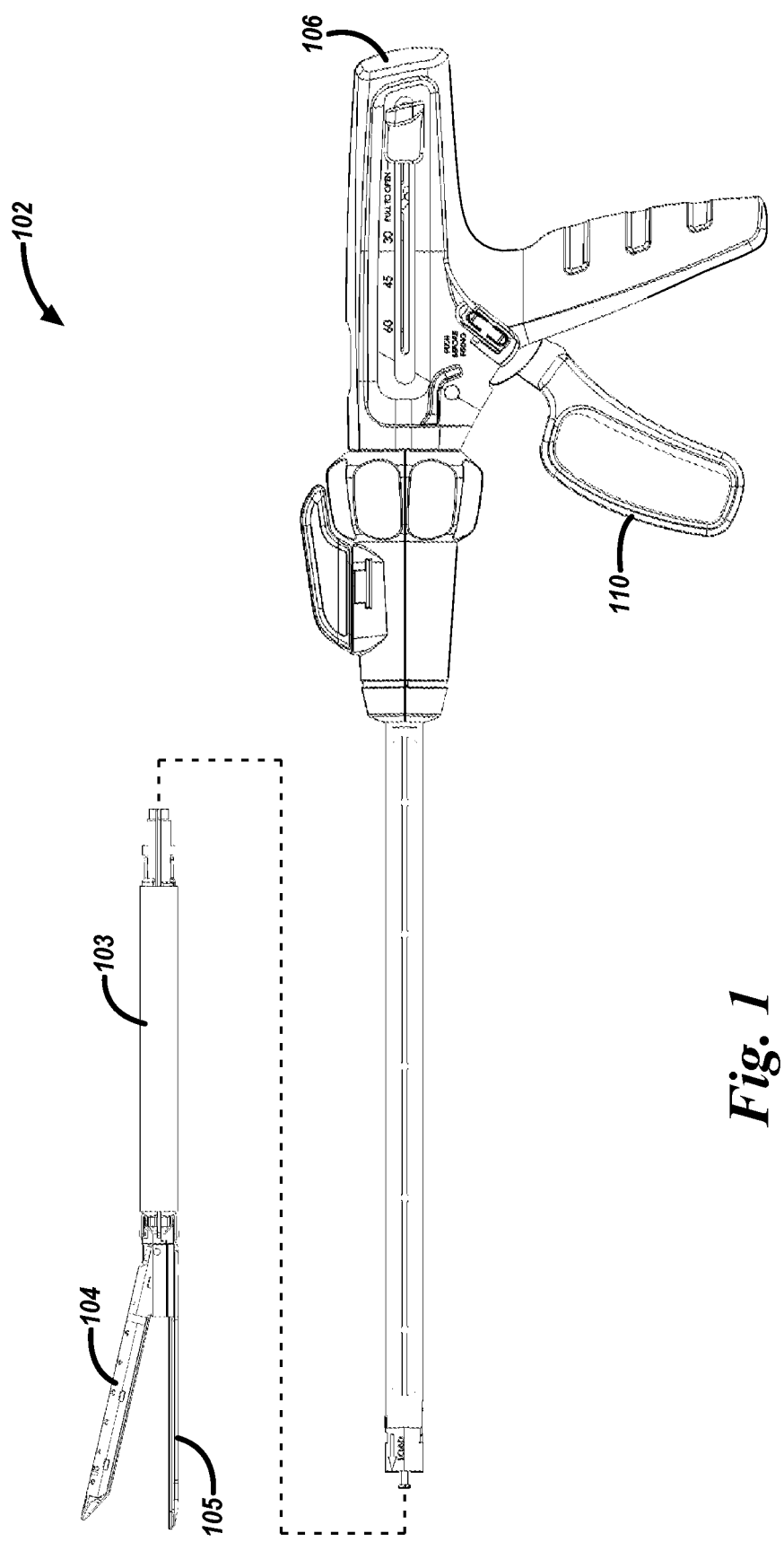
FIG. 1 is a schematic diagram of a surgical stapling apparatus including a surgical reloadable cartridge assembly in accordance with a number of embodiments of the present disclosure.

The present disclosure includes apparatuses for a surgical reloadable cartridge assembly. An example apparatus includes a lock slider and a blade lock configured to actuate radially between a first position that locks a blade in a secure position and a second position that allows the blade to move longitudinally. The blade lock can actuate radially in response to longitudinal movement of the lock slider.

In a number of embodiments, the lock slider is configured to move distally. When the lock slider moves distally it can engage the blade lock. The blade lock engaged by the lock slider can actuate radially. In a number of embodiments, the blade lock can actuate radially outward. When the blade lock is actuated radially outward, for example, the blade lock can move from a first position to a second position. In this example, the blade lock can move radially between the first position and the second position in response to longitudinal movement of the lock slider.

In a number of embodiments, a spring can be configured to bias the lock slider. For example, the spring can bias the lock slider in a proximal direction. The spring biasing the lock slider in a proximal direction can cause the lock slider to engage the blade lock. The lock slider, when biased by the spring, can engage the blade lock to place the blade lock in a secure position in an opening in the blade. A spring is used throughout the present disclosure to describe biasing the lock slider for ease of understanding and illustration; however embodiments are not limited to using a spring to bias the lock slider.

In a number of embodiments, the lock slider can engage the blade lock to bias the blade lock in a first position. The first position, for example, can be a secure position. The blade lock can be in a first position, e.g. secure position, when the blade lock is between the blade and the lock slider, for example. The secure position can be a position that prevents the blade from moving, e.g. locks the blade. The secure position can also be a position where the blade is enclosed by a cover of a surgical reloadable cartridge assembly. In this example, the blade may be in a secure position when the surgical reloadable cartridge assembly is being transported, e.g. carried and/or shipped, and/or stored.

In a number of embodiments, the blade lock can be in a second position. The second position, for example, can be an open position. The blade lock can be in a second position, e.g. open position, when the blade lock is above, e.g. not in an opening of the blade, the blade. The open position can be a position that allows the blade to move longitudinally. In this example, the blade may be in an open position when the surgical reloadable cartridge assembly is in use. The surgical reloadable cartridge assembly can be in use when the surgical reloadable cartridge assembly is connected to a movable handle assembly, for example.

In a number of embodiments, the lock slider can be configured to move proximally. When the lock slider moves proximally, the lock slider can engage the blade lock to actuate the blade lock radially. In a number of embodiments, the blade lock can actuate radially inward towards a center of the surgical reloadable cartridge assembly. When the blade lock is actuated radially inward, for example, the blade lock can move from a second position to a first position. In this example, the blade lock can move radially between the second position and the first position in response to longitudinal movement of the lock slider.

In a number of embodiments, the blade lock can actuate radially from the first position to the second position in response to coupling the surgical reloadable cartridge assembly to a movable handle assembly. The movable handle assembly can engage the lock slider of the surgical reloadable cartridge assembly. The engagement of the movable handle assembly with the lock slider can overcome the bias created by the spring to allow the lock slider to move in a distal direction. When the lock slider moves in the distal direction, the lock slider can engage the blade lock to actuate radially to a second position. The blade lock in the second position can allow the blade to move longitudinally. The blade may be used when the surgical reloadable cartridge assembly is coupled to a movable handle assembly, for example.

In a number of embodiments, a surgical stapler can include the surgical reloadable cartridge assembly. The secure position of the locked blade when the blade lock is in the second position can be inside the surgical reloadable cartridge assembly. For example, the blade can be encapsulated by a cover of the surgical reloadable cartridge assembly. The lock slider and the blade lock, for example, can be encapsulated by a sleeve of the surgical reloadable cartridge assembly regardless of whether the blade lock is in a first position or a second position.

In a number of embodiments, the surgical reloadable cartridge assembly can include a blade with an opening. The surgical reloadable cartridge assembly can also include a lock slider and a blade lock. The lock slider can include a first incline plane, a second incline plane, a fifth incline plane, and a sixth incline plane. The blade lock can include a third incline plane, a fourth incline plane, a seventh incline plane, and an eighth incline plane. The blade lock can be positioned in the opening of the blade to prevent movement of the blade. The blade lock can prevent movement of the blade, for example, when the third incline plane of the blade lock is in contact with the first incline plane of the lock slider and/or when the seventh incline plane of the blade lock is in contact with the fifth incline plane of the lock slider.

In a number of embodiments, the blade lock can be positioned outside of the opening of the blade. When the blade lock is positioned outside of the opening of the blade the blade is allowed to move. For example, the blade can move when the second incline plane of the lock slider is in contact with the fourth incline plane of the blade lock and/or when the sixth incline plane of the lock slider is in contact with the eighth incline plane of the blade lock.

In a number of embodiments the opening of the blade may have a first edge and a second edge. In this example, the blade lock can have a first sidewall and a second sidewall. In a number of embodiments, the first edge of the opening can contact the first sidewall of the blade lock to prevent distal movement of the blade. The second edge of the opening can contact a second sidewall of the blade lock, for example, to prevent proximal movement of the blade. When the blade cannot move, the blade lock can be in a first, e.g. secure, position, for example.

In a number of embodiments, a surgical reloadable cartridge assembly may comprise an articulation arm, a sleeve, and a cover. The articulation arm can actuate a first elongated member and/or a second elongated member of the surgical reloadable cartridge assembly. For example, the articulation arm can be used to actuate the surgical reloadable cartridge assembly to access tissue.

In a number of embodiments, the sleeve of the surgical reloadable cartridge assembly can prevent the articulation arm from moving in more than one direction, e.g. only in the longitudinal direction. For example, the sleeve can prevent the articulation arm from moving past an outer surface of the surgical reloadable cartridge assembly.

In a number of embodiments, the cover may include a first portion with a post and a second portion with a cavity. The first portion of the cover with the post and the second portion of the cover with the cavity can be configured to prevent the articulation arm from moving in more than one direction. For example, the first portion of the cover with the post and the second portion of the cover with the cavity may allow the articulation arm to move in a longitudinal direction.

In a number of embodiments, the post of the first portion of the cover may mate with the cavity of the second portion of the cover in response to the first portion of the cover and the second portion of the cover being coupled together. When the first portion of the cover and the second portion of the cover are coupled together, the first portion of the cover and the second portion of the cover can prevent the articulation arm from moving towards a center of the surgical reloadable cartridge assembly.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process and structural changes may be made without departing from the scope of the present disclosure.

It is to be understood that the terminology used herein is for the purpose of describing particular embodiments only, and is not intended to be limiting. As used herein, the singular forms "a", "an", and "the" can include both singular and plural referents, unless the context clearly dictates otherwise. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the surgical reloadable cartridge assembly, as appropriate to the context.

The figures herein follow a numbering convention in which the first digit or digits correspond to the figure number and the remaining digits identify an element or component in the figure. Similar elements or components between different figures may be identified by the use of similar digits. For example, 212 may reference element "12" in FIG. 2, and a similar element may be referenced as 312 in FIG. 3A. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a schematic diagram of a surgical stapling apparatus 102 including a surgical reloadable cartridge assembly 103 in accordance with a number of embodiments of the present disclosure. In the example, a surgical stapler apparatus 102 can include a surgical reloadable cartridge assembly 103, e.g. a disposable loading unit, and a surgical handle assembly 106. The surgical reloadable cartridge assembly 103 can be releasably secured to a distal end of an elongated body of the surgical handle assembly 106. In this example, the surgical reloadable cartridge assembly 103 can include a first elongated member 104 and a second elongated member 105 that can be used to clamp tissue. One of the elongated members can house one or more staple cartridges. The other elongated member can have an anvil that can be used to form a staple when driven from the staple cartridge.

As mentioned, a surgical stapling apparatus 102 can receive surgical reloadable cartridge assemblies having rows of staples. In a number of embodiments, third party surgical reloadable cartridge and/or surgical reloadable cartridge assemblies may be used with the surgical handle assembly 106 and embodiments of surgical handle assembly 106 may be configured to receive the same. A staple can be ejected by actuation of a movable handle member 110 that is a part of the surgical handle assembly 106 to the surgical stapling apparatus 102. Actuation of the movable handle member 110 can actuate the blade (e.g. blade 216 in FIG. 2) to eject a number of staples and cut. Further, embodiments are not limited to use with a surgical stapling apparatus. The surgical handle assembly 106 is described with the surgical stapling apparatus 102 example throughout the present disclosure for ease of understanding and illustration.

Figure 2:
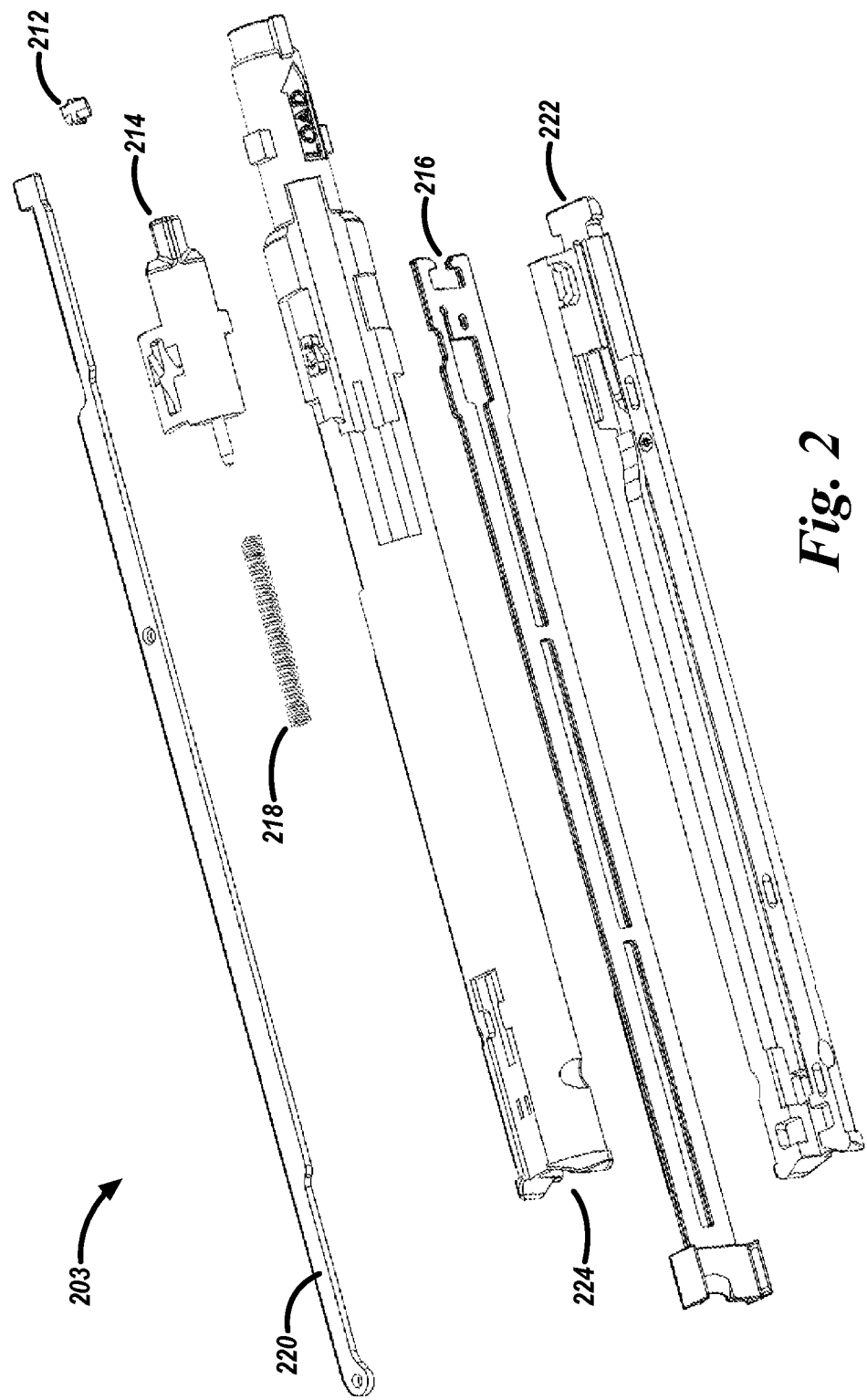
FIG. 2 is an exploded view schematic diagram of a surgical reloadable cartridge assembly in accordance with a number of embodiments of the present disclosure.

FIG. 2 is an exploded view schematic diagram of a surgical reloadable cartridge assembly in accordance with a number of embodiments of the present disclosure. The surgical reloadable cartridge assembly 203 can include a blade lock 212, a lock slider 214, a spring 218, an articulation arm 220, a first portion of a cover 224, a second portion of the cover 222, and a blade 216.

In a number of embodiments, the lock slider 214 is configured to move distally to engage the blade lock 212 and actuate the blade lock 212 radially from the first position to the second position. The blade lock 212 can move radially between a first position and a second position without rotational movement, e.g. the lock slider 214 and/or blade lock 212 do not move rotationally. The spring 218 can be configured to bias the lock slider 214 in a proximal direction so the lock slider 214 is engaged with the blade lock 212 and the blade lock 212 is in the first position. The first position, for example, can be a secure position that locks the blade 216. The blade 216 can be locked when the blade lock 212 is between the blade 216 and the lock slider 214.

In a number of embodiments, the lock slider 214 can be configured to move proximally to engage the blade lock 212 and actuate the blade lock 212 from the second position to the first position. The blade lock 212 can actuate radially to the second position in response to the lock slider 214 moving in a distal direction when the assembly is coupled to a movable handle assembly (e.g. movable handle assembly 106 in FIG. 1). For example, the blade 216 can be unlocked when the lock slider 214 is between the blade 216 and the blade lock 212.

In a number of embodiments, a surgical stapler can include the surgical reloadable cartridge assembly 203. The secure position of the locked blade 216 can be inside the surgical reloadable cartridge assembly 203. For example, the blade 216 can be encapsulated by a first portion of a cover (e.g. first portion of a cover 524 in FIG. 5) and a second portion of the cover (e.g. second portion of the cover 522 in FIG. 5).

FIG. 3A is a schematic diagram of a surgical reloadable cartridge assembly including a blade lock in a first position in accordance with a number of embodiments of the present disclosure. The surgical reloadable cartridge assembly 303 can include a blade lock 312, a lock slider 314, a blade 316, and a spring 318.

In a number of embodiments, the lock slider 314 is configured to move distally to engage the blade lock 312 and actuate the blade lock 312 radially from the first position to the second position. The blade lock 312 can move radially between a first position and a second position in response to longitudinal movement of the lock slider 314. A spring 318 can be configured to bias the lock slider 314 in a proximal direction so the lock slider 314 is engaged with the blade lock 312 and the blade lock 312 is in the first position. The first position, for example, can be a secure position that locks the blade 316. The blade 316 can be locked when the blade lock 312 is between the blade 316 and the lock slider 314.

FIG. 3B is a section view schematic diagram of a surgical reloadable cartridge assembly including a blade lock in a first position in accordance with a number of embodiments of the present disclosure. The surgical reloadable cartridge assembly 303 can include a blade lock 312, a lock slider 314, a blade 316, and a spring 318.

Figure 4A:
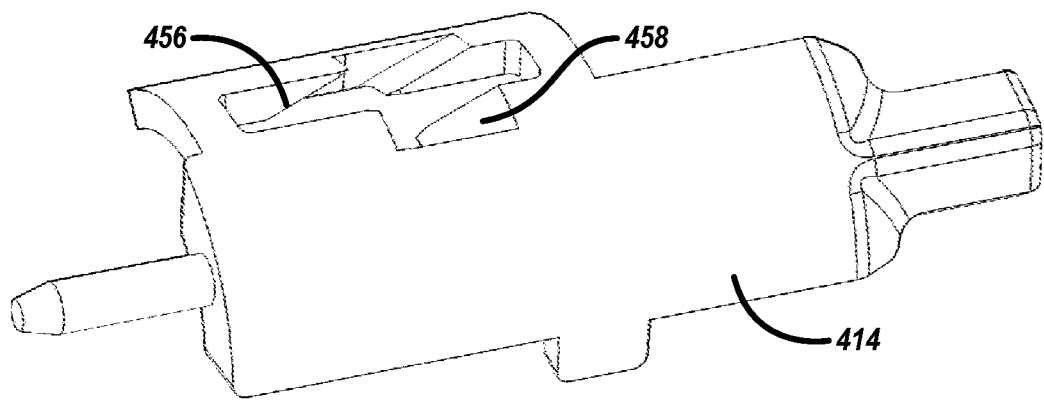
FIG. 4A is a schematic diagram of a blade lock and a lock slider of a surgical reloadable cartridge assembly in accordance with a number of embodiments of the present disclosure.
Figure 4B:
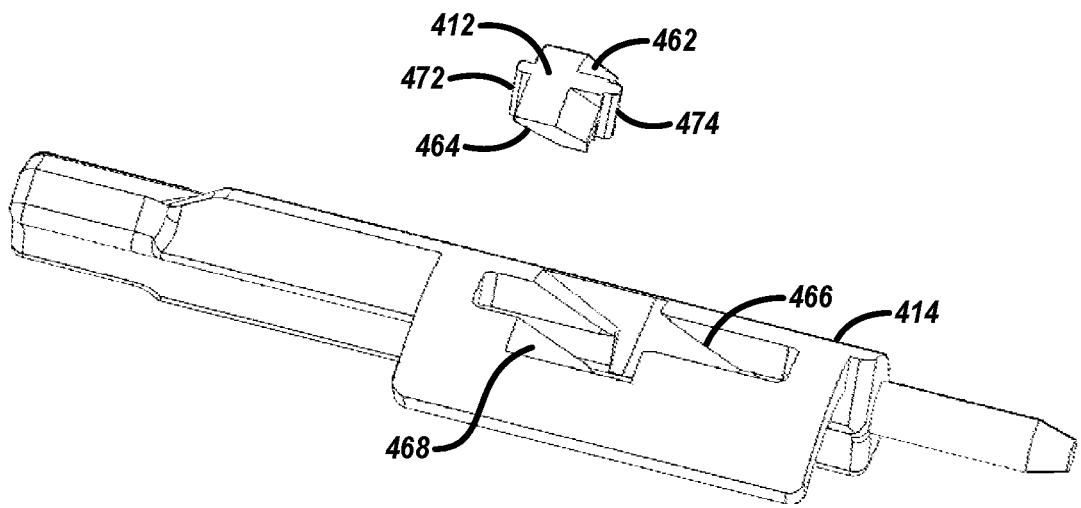
FIG. 4B is a schematic diagram of a blade lock and a lock slider of a surgical reloadable cartridge assembly in accordance with a number of embodiments of the present disclosure.

In a number of embodiments, the surgical reloadable cartridge assembly 303 can include a blade 316 including an opening 317 and a lock slider 314 including a first incline plane (e.g. first incline plane 456 in FIG. 4A), a second incline plane (e.g. second incline plane 458 in FIG. 4A), a fifth incline plane (e.g. incline plane 466 in FIG. 4B), and a sixth incline plane (e.g. incline plane 468 in FIG. 4B). The surgical reloadable cartridge 303 can also include a blade lock 312 including a third incline plane (e.g. incline plane 452 in FIG. 4A), a fourth incline plane (e.g. incline plane 454 in FIG. 4A), a seventh incline plane (e.g. incline plane 462 in FIG. 4B), and an eighth incline plane (e.g. incline plane 464 in FIG. 4B). The blade lock 312 can be positioned in the opening 317 of the blade to prevent movement of the blade, e.g. a first position, when the third incline plane of the blade lock 312 is in contact with the first incline plane of the lock slider 314 and/or when the seventh incline plane of the blade lock 312 is in contact with the fifth incline plane of the lock slider 314.

In a number of embodiments, a first edge 319 of the opening can contact a first sidewall (e.g. first sidewall 472 in FIG. 4A) of the blade lock 312 to prevent distal movement of the blade 316 and a second edge 315 of the opening 317 can contact a second sidewall (e.g. second sidewall 474 in FIG. 4A) of the blade lock 312 to prevent proximal movement of the blade 316.

FIG. 3C is a schematic diagram of a surgical reloadable cartridge assembly including a blade lock in a second position in accordance with a number of embodiments of the present disclosure. The surgical reloadable cartridge assembly 303 can include a blade lock 312, a lock slider 314, a blade 316, and a spring 318.

In a number of embodiments, the lock slider 314 can be configured to move distally to engage the blade lock 312 and actuate the blade lock 312 from the first position to the second position. The blade lock 312 can actuate radially to the second position in response to the lock slider 314 moving in a distal direction when the assembly is coupled to a movable handle assembly (e.g. movable handle assembly 106 in FIG. 1). For example, the blade 316 can be unlocked when the lock slider 314 is between the blade 316 and the blade lock 312.

FIG. 3D is a section view schematic diagram of a surgical reloadable cartridge assembly including a blade lock in a second position in accordance with a number of embodiments of the present disclosure. The surgical reloadable cartridge assembly 303 can include a blade lock 312, a lock slider 314, a blade 316, and a spring 318.

In a number of embodiments, the blade lock 312 can be positioned outside of the opening of the blade 316, e.g. a second position, to allow movement of the blade 316 when the second incline plane (e.g. incline plane 458 in FIG. 4A) of the lock slider 314 is in contact with the fourth incline plane (e.g. incline plane 454 in FIG. 4A) of the blade lock 312 and/or when the sixth incline plane (e.g. incline plane 468 in FIG. 4B) of the lock slider 314 is in contact with the eighth incline plane (e.g. incline plane 464 in FIG. 4B) of the blade lock 312.

FIG. 4A is a schematic diagram of a blade lock and a lock slider of a surgical reloadable cartridge assembly in accordance with a number of embodiments of the present disclosure. The blade lock 412 can include a first sidewall 472 and a second sidewall 474. In a number of embodiments, the first edge (e.g. edge 319 in FIG. 3A) of the opening (e.g. opening 317 in FIG. 3A) of the blade (e.g. blade 316 in FIG. 3A) can contact the first sidewall 472 of the blade lock 412 to prevent distal movement of the blade. Proximal movement of the blade may also be prevented. The second edge (e.g. edge 315 in FIG. 3A) of the opening can contact a second sidewall 474 of the blade lock 412, for example, to prevent proximal movement of the blade. When the blade cannot move, the blade lock 412 can be in a first position, for example.

In a number of embodiments, the surgical reloadable cartridge assembly (e.g. surgical reloadable cartridge assembly 303 in FIG. 3A) can include a lock slider 414. The lock slider 414 can include a first incline plane 456 and a second incline plane 458. The surgical reloadable cartridge assembly can also include a blade lock 412. The blade lock 412 can include a third incline 452 plane and a fourth incline plane 454. The blade lock 412 can be positioned in the opening (e.g. opening 317 in FIG. 3A) of the blade (e.g. blade 316 in FIG. 3A) to prevent movement of the blade. The blade lock 412 can prevent movement of the blade, for example, when the third incline plane 452 of the blade lock 412 is in contact with the first incline plane 456 of the lock slider 414.

In a number of embodiments, the blade lock 412 can be positioned outside of the opening (e.g. opening 317 in FIG. 3A) of the blade (e.g. blade 316 in FIG. 3A). When the blade lock 412 is positioned outside of the opening of the blade the blade is allowed to move. For example, the blade can move when the second incline plane 458 of the lock slider 414 is in contact with the fourth incline plane 454 of the blade lock 412. When the blade can move, the blade lock 412 can be in a second position, for example.

FIG. 4B is a schematic diagram of a blade lock and a lock slider of a surgical reloadable cartridge assembly in accordance with a number of embodiments of the present disclosure. The blade lock 412 can include a first sidewall 472 and a second sidewall 474. In a number of embodiments, the first edge (e.g. edge 319 in FIG. 3A) of the opening (e.g. opening 317 in FIG. 3A) of the blade (e.g. blade 316 in FIG. 3A) can contact the first sidewall 472 of the blade lock 412 to prevent distal movement of the blade. Proximal movement of the blade may also be prevented. The second edge (e.g. edge 315 in FIG. 3A) of the opening can contact a second sidewall 474 of the blade lock 412, for example, to prevent proximal movement of the blade. When the blade cannot move, the blade lock 412 can be in a first position, for example.

In a number of embodiments, the surgical reloadable cartridge assembly (e.g. surgical reloadable cartridge assembly 303 in FIG. 3A) can include a lock slider 414. The lock slider 414 can include a fifth incline plane 466 and a sixth incline plane 468. The surgical reloadable cartridge assembly can also include a blade lock 412. The blade lock 412 can include a seventh incline 462 plane and an eighth incline plane 464. The blade lock 412 can be positioned in the opening (e.g. opening 317 in FIG. 3A) of the blade (e.g. blade 316 in FIG. 3A) to prevent movement of the blade. The blade lock 412 can prevent movement of the blade, for example, when the incline plane 462 of the blade lock 412 is in contact with the incline plane 466 of the lock slider 414 and/or when the incline plane (e.g. incline plane 452 in FIG. 4A) of the blade lock 412 is in contact with the first incline plane (e.g. incline plane 456 in FIG. 4A) of the lock slider 414.

In a number of embodiments, the blade lock 412 can be positioned outside of the opening (e.g. opening 317 in FIG. 3A) of the blade (e.g. blade 316 in FIG. 3A). When the blade lock 412 is positioned outside of the opening of the blade, the blade is allowed to move. For example, the blade can move when the sixth incline plane 468 of the lock slider 414 is in contact with the eighth incline plane 464 of the blade lock 412 and/or when the second incline plane (e.g. incline plane 458 in FIG. 4A) of the lock slider 414 is in contact with the fourth incline plane (e.g. incline plane 454 in FIG. 4) of the blade lock 412. When the blade can move, the blade lock 412 can be in a second position, for example.

Figure 5A:
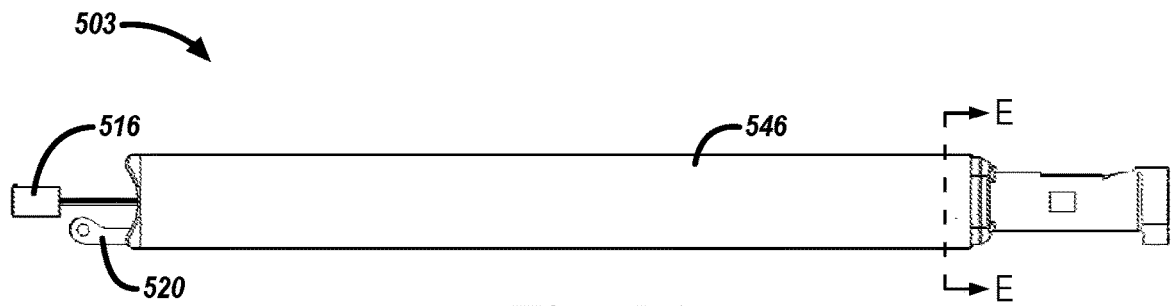
FIG. 5A is a schematic diagram of a surgical reloadable cartridge assembly in accordance with a number of embodiments of the present disclosure.

FIG. 5A is a schematic diagram of a surgical reloadable cartridge assembly in accordance with a number of embodiments of the present disclosure. The surgical reloadable cartridge assembly 503 can include a blade 516, an articulation arm 520, and a sleeve 546.

In a number of embodiments, the articulation arm 520 can actuate jaw structures including a first elongated member (e.g. first elongated member 104 in FIG. 1) and/or a second elongated member (e.g. second elongated member 105) of the surgical reloadable cartridge assembly 503. For example, the articulation arm 520 can be used to pivot the surgical reloadable cartridge assembly 503 to clamp tissue.

In a number of embodiments, the surgical reloadable cartridge assembly 503 can also include a sleeve 546. The sleeve 546 can prevent the articulation arm 520 from moving in more than one direction. For example, the sleeve can prevent the articulation arm 520 from moving past an outer surface of the surgical reloadable cartridge assembly 503.

Figure 5B:
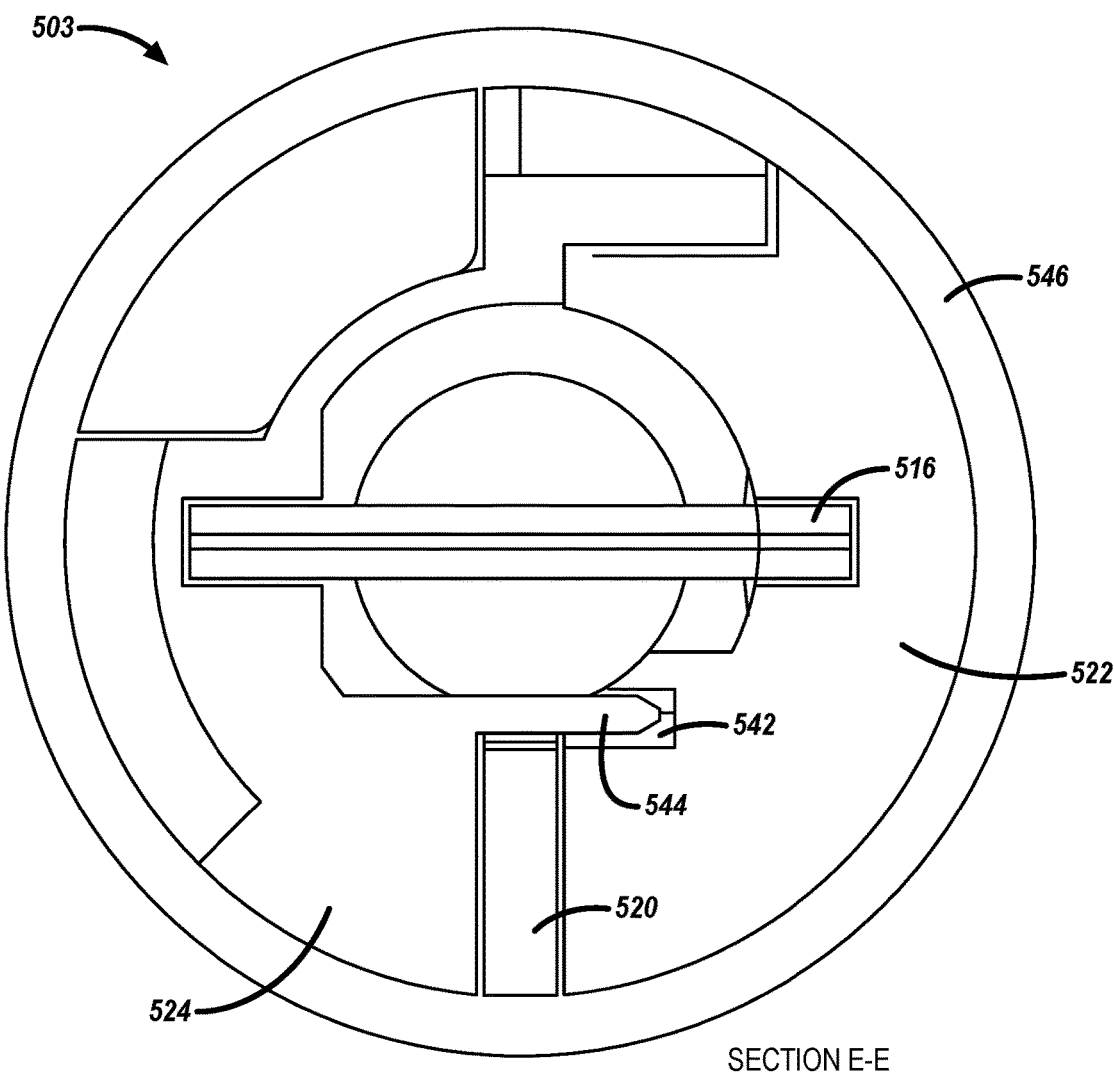
FIG. 5B is a section view schematic diagram of a surgical reloadable cartridge assembly in accordance with a number of embodiments of the present disclosure.

FIG. 5B is a section view schematic diagram of a surgical reloadable cartridge assembly in accordance with a number of embodiments of the present disclosure. The surgical reloadable cartridge assembly 503 can include a blade 516, an articulation arm 520, a sleeve 546, a first portion of a cover 524, and a second portion of a cover 522. The first portion of the cover 524 can include a post 544 and the second portion of the cover 522 can include a cavity 542.

In a number of embodiments, the first portion of the cover 524 with the post 544 and the second portion of the cover 522 with the cavity 542 can be configured to prevent the articulation arm 520 from moving in more than one direction. For example, the first portion of the cover 524 with the post 544 and the second portion of the cover 522 with the cavity 542 may allow the articulation arm 520 to move in a longitudinal direction.

In a number of embodiments, the post 544 of the first portion of the cover 524 can mate with the cavity 542 of the second portion of the cover 522 in response to the first portion of the cover 524 and the second portion of the cover 522 being coupled together. When the first portion of the cover 524 and the second portion of the cover 522 are coupled together the first portion of the cover 524 and the second portion of the cover 522 can prevent the articulation arm 520 from moving towards a center of the surgical reloadable cartridge assembly 503.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A surgical reloadable cartridge assembly apparatus, comprising:
   an articulation arm;
   a sleeve; and
   a cover including a first portion with a post and a second portion with a cavity, wherein the first portion of the cover, the post, the second portion of the cover, and the sleeve define a passage configured to allow movement of the articulation arm in a longitudinal direction and prevent the articulation arm from moving in any other direction.

2. The apparatus of claim 1, wherein the post mates with the cavity in response to the first portion and the second portion being coupled together to prevent the articulation arm from moving towards a center of the surgical reloadable cartridge assembly.

3. The apparatus of claim 1, wherein the articulation arm actuates jaw structures.

4. The apparatus of claim 1, wherein the sleeve prevents the articulation arm from moving past an outer surface of the surgical reloadable cartridge assembly.

5. The apparatus of claim 1, wherein the sleeve encapsulates the first portion and the second portion of the cover.

6. The apparatus of claim 1, further comprising a blade.

7. The apparatus of claim 6, wherein the first portion and the second portion of the cover encapsulate the blade.

8. A surgical reloadable cartridge assembly apparatus, comprising:
   an articulation arm;
   a sleeve; and
   a cover including a first portion with a post and a second portion with a cavity, wherein the first portion of the cover, the post, the second portion of the cover, and the sleeve define a passage configured to allow movement of the articulation arm in a longitudinal direction and prevent the articulation arm from moving in any other direction, and wherein
   the sleeve is configured to encapsulate the articulation arm and the cover.

9. The apparatus of claim 8, wherein the cover allows movement of the articulation arm in the longitudinal direction and prevents the articulation arm from moving in any other direction in response to the post of the first portion of the cover mating with the cavity of the second portion of the cover and the sleeve encapsulating the articulation arm and the cover.

10. The apparatus of claim 8, wherein movement of the articulation arm pivots the surgical reloadable cartridge assembly.

11. The apparatus of claim 10, wherein the surgical reloadable cartridge assembly clamps tissue after the articulation arm pivots the surgical reloadable cartridge assembly.

12. A surgical reloadable cartridge assembly apparatus, comprising:
   a sleeve; and
   a cover including a first portion with a post and a second portion with a cavity, wherein the first portion of the cover, the post, the second portion of the cover, and the sleeve define a passage configured to allow movement of an articulation arm in a longitudinal direction and prevent the articulation arm from moving in any other direction, and wherein
   the sleeve is configured to encapsulate the first portion and the second portion of the cover, wherein the cover and the sleeve prevents a blade from moving past an outer surface of the surgical reloadable cartridge assembly.

13. The apparatus of claim 12, wherein the blade is configured to form an incision in tissue.

14. The apparatus of claim 12, wherein the blade is configured to cut stapled tissue.

15. The apparatus of claim 12, wherein the surgical reloadable cartridge assembly is coupled to a movable handle assembly.

16. The apparatus of claim 15, wherein the blade is configured to actuate in response to actuation of a movable handle member of the movable handle assembly.

17. The apparatus of claim 12, wherein the cover and the sleeve prevent the articulation arm from moving past the outer surface of the surgical reloadable cartridge assembly.

* * * * *